(12) United States Patent
Schneider et al.

(10) Patent No.: US 7,560,592 B2
(45) Date of Patent: *Jul. 14, 2009

(54) ACTIVE AROMATIC SULFONAMIDE ORGANIC COMPOUNDS AND BIOCIDAL USES THEREOF

(75) Inventors: Charles A. Schneider, Villa Hills, KY (US); David J. Schneider, Union, KY (US)

(73) Assignee: SAT, Inc., Union, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/506,737

(22) Filed: Aug. 18, 2006

(65) Prior Publication Data

US 2006/0280766 A1 Dec. 14, 2006

Related U.S. Application Data

(63) Continuation-in-part of application No. 11/216,495, filed on Aug. 31, 2005, which is a continuation-in-part of application No. 10/369,175, filed on Feb. 18, 2003, now Pat. No. 7,465,829.

(60) Provisional application No. 60/709,919, filed on Aug. 19, 2005, provisional application No. 60/357,265, filed on Feb. 19, 2002.

(51) Int. Cl.
*C07D 303/00* (2006.01)
*C07D 255/00* (2006.01)

(52) U.S. Cl. .............................. 564/84; 564/90; 564/99; 558/413

(58) Field of Classification Search ................. 558/413; 504/99, 84, 90
See application file for complete search history.

(56) References Cited

U.S. PATENT DOCUMENTS

| | | | | |
|---|---|---|---|---|
| 2,809,937 | A | * 10/1957 | Gray | .......................... 510/382 |
| 5,710,101 | A | 1/1998 | Carstairs et al. | |
| 5,952,359 | A | 9/1999 | Godfrey et al. | |
| 6,296,841 | B1 | * 10/2001 | Schneider | .................. 424/76.1 |

OTHER PUBLICATIONS

FDA, Dry Milk Ordinance Supplement 1 Appendix B pp. 87-88 (1995).*
Mullen, The Biocides Business: Regulation, Safety and Applications, pp. 251-266, (2002).*
Dawson et al, Inter. Ass. Fish & Wildlife, Approval of Drugs for Public fish Production, Second Mids-Year Report of Progress, pp. 1-11.*
Chrzasczewska et al PL 52046( CA 69:18848 Best Available).*

* cited by examiner

*Primary Examiner*—Janet L. Andres
*Assistant Examiner*—Raymond Covington
(74) *Attorney, Agent, or Firm*—Richard M. Klein; Fay Sharpe LLP

(57) ABSTRACT

A biocidal solution comprising aromatic N-halosulfonamide organic compounds and methods of using the biocidal solution are disclosed. The solution may further comprise a wetting agent, a low molecular weight alcohol, and buffering agents. The biocidal solution is used to arrest or kill unwanted organisms.

19 Claims, No Drawings

ACTIVE AROMATIC SULFONAMIDE ORGANIC COMPOUNDS AND BIOCIDAL USES THEREOF

CROSS-REFERENCE TO RELATED APPLICATIONS

The present application claims priority to U.S. Provisional Application Ser. No. 60/709,919, filed on Aug. 19, 2005, for "New Benzene Sulfonamide Biocidal Formulations." This application is also a continuation-in-part application of currently pending U.S. patent application Ser. No. 11/216,495, filed on Aug. 31, 2005, for "Halo Active Aromatic Sulfonamide Organic Compounds and Odor Control Uses Thereof". That application is, in turn, a continuation-in-part application of U.S. application Ser. No. 10/369,175, filed Feb. 18, 2003 now U.S. Pat. No. 7,465,829, which application claims priority of Provisional Application Ser. No. 60/357,265, filed Feb. 19, 2002.

BACKGROUND

This disclosure relates to uses of halo active aromatic sulfonamide organic compounds which have enhanced biocidal properties and minimal side effects. In a broad context, this disclosure concerns the use of halo active sulfonamide compounds to arrest or kill the growth of living organisms, particularly microorganisms. It may also be used as a fungicide or pesticide.

When the halo active aromatic sulfonamide compounds of this disclosure are used, solutions of the sulfonamide compound are brought into contact with an area affected by microorganisms. This contact is usually affected by spraying, washing, dipping, and/or mixing in such a manner as to contact the affected area, surface, or substrate with an aqueous formulation of the desired sulfonamide compound or a blended mixture of same.

REFERENCES

U.S. Pat. No. 6,296,841 relates to the use of Chloramine-T, a sulfonamide, as an odor control agent wherein the Chloramine-T is used with a wetting agent. The disclosure relates primarily to domestic odor control.

U.S. Pat. No. 6,743,420 describes the use of Chloramine-T as an odor control agent wherein the Chloramine-T is used with and without a wetting agent. The disclosure of this patent relates to domestic and industrial odor control.

U.S. Pat. No. 6,667,030 further relates to the use of Chloramine T as an odor control agent.

BRIEF DESCRIPTION

Disclosed herein, in various embodiments, are biocidal solutions comprising halo active aromatic sulfonamide organic compounds suitable for use as biocides. Processes for using the solutions are also disclosed. The solutions may further comprise a wetting agent and a low molecular weight alcohol.

Also disclosed are processes for arresting or killing unwanted microorganisms on an affected area by treating the area with the solution. The solution may be sprayed, swabbed, or vapor contacted. Alternatively, the solution may be incorporated into a soap, lotion, wipe, swab, bath, medical device, dressing, or the like.

These and other non-limiting features or characteristics of the present disclosure will be further described below.

DETAILED DESCRIPTION

The halo active aromatic sulfonamide compounds as used in this application exhibit enhanced biocidal properties. In addition many of these compounds have very low toxicity properties which make them attractive for use around human, animal and aquatic environments.

The halo active aromatic sulfonamide compounds suitable for use in the solutions of the present application may be selected from the following Formulas I-IV:

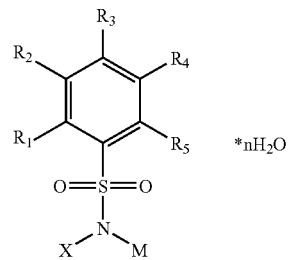

Formula I wherein

X is a halogen;

$R_3$ is hydrogen, methyl, or COOM;

$R_1$, $R_2$, $R_4$, and $R_5$ are independently selected from hydrogen, $CF_3$, COOH, derivatized COOH, an ester or alkylated amide, COOM, CN, $NO_2$, $SO_3H$ or derivatized $SO_3R$, a halogen, a substituted or unsubstituted phenyl group, a sulfonamide, a halosulfonamide, and a straight or branched aliphatic moiety from $C_1$ to $C_{12}$, wherein the same straight or branched aliphatic moiety may be substituted at one or more of the aliphatic hydrogens;

at least one of $R_1$, $R_2$, $R_4$ and $R_5$ is not hydrogen; and

M is an alkali or alkaline earth metal;

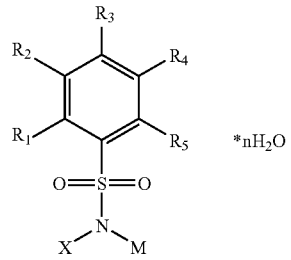

Formula II wherein

X is a halogen;

$R_1$, $R_2$, $R_3$, $R_4$, and $R_5$ are independently selected from hydrogen, $CF_3$, COOH, derivatized COOH, an ester or alkylated amide, COOM, CN, $NO_2$, $SO_3H$ or derivatized $SO_3R$, a halogen, a substituted or unsubstituted phenyl group, a sulfonamide, a halosulfonamide, a straight or branched aliphatic moiety from $C_1$ to $C_{12}$, wherein the same straight or branched aliphatic moiety may be substituted at one or more of the aliphatic hydrogens;

wherein $R_3$ is not hydrogen; and

M is an alkali or alkaline earth metal;

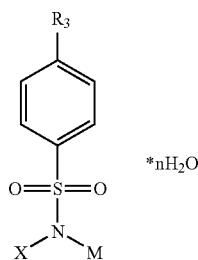

Formula III wherein
X is a halogen;
$R_3$ is hydrogen, methyl, or COOM; and
M is selected from potassium, rubidium, cesium, lithium or an alkaline earth metal; and,

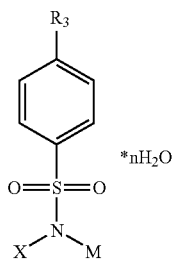

Formula IV wherein
X is bromine, fluorine, or iodine;
$R_3$ is hydrogen, methyl, or COOM; and
M is an alkali or alkaline earth metal.

Compounds of Formulas I-IV may or may not be hydrated (n $H_2O$), but are generally isolated as a trihydrate (where n=3). The compounds of Formulas I-IV are very soluble in water. This property allows for easy compounding of biocidal solutions and allows high percentages of the compounds to be formulated into useful solution products. Furthermore, these compounds have minimal bleach odor. This property is highly advantageous because formulations with strong bleach odor are undesirable in many applications. These compounds have also been found to be stable in the 45-50° C. range for greater than 6 months in water at various concentrations.

The alkali metal salts of N-halo-4-carboxybenzene sulfonamides in particular have been found to be particularly outstanding biocides. These sulfonamides are shown in Formula V:

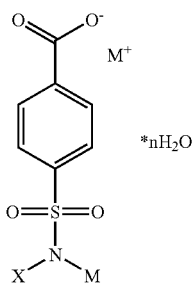

Formula V wherein
X is a halogen; and
M is an alkali or alkaline earth metal.

In specific embodiments of Formula V, M is sodium or potassium; and X is chlorine. The salts in the dry state are hydrated. The chemical structures of these specific salts are shown in Formulas VI and VII:

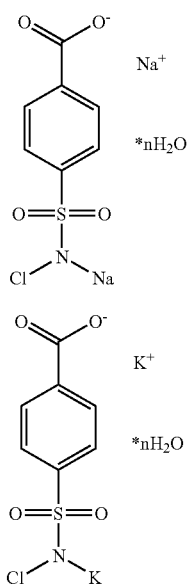

Formula VI

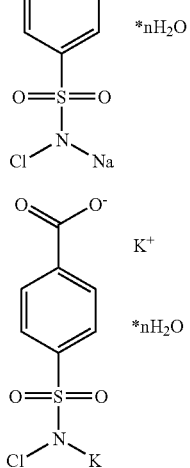

Formula VII

The salts of Formula V have been found to be useful biocides at concentrations of from about 0.01 to about 37% in water. (All concentrations in this application should be interpreted as wt/wt.) Especially useful concentrations are from about 0.1 to about 20%. Water is also preferred as a solvent for the sulfonamide salts of the present application.

These alkali metal salts have been found to function as biocides with minimal undesirable side effects. A particularly beneficial property is the fact that these salts are nontoxic to humans, but toxic to the unwanted organisms. As a result of this nontoxicity, the salts in question can be used in proximity to humans with generally no ill effects. Tests showed that the disodium salts of N-chloro-4-carboxybenzene sulfonamide formulations had zero kill when attempting to establish $LD_{50}$, and hence they are classified as nontoxic to humans.

In further specific embodiments of the present application, the biocidal solution comprises a wetting agent. The wetting agent aids in placement and functioning of the biocide by ensuring that the sulfonamide salt is able to contact the organism it is being used to kill.

An additional aspect of this application is concerned with the fact that many wetting agents may adversely affect the formation of the Cl+ moiety, from the compounds of Formulas I-IV, or degrade said Cl+ moiety once it is formed. Both synthetic and natural wetting agents exist. They are generally classified as cationic, anionic, amphoteric and nonionic. Nonionic wetting agents are generally preferred for use in the biocidal solution. However, satisfactory agents may be found in any class of wetting agents.

One especially suitable wetting agent for use in the biocidal solution of the present application is an anionic wetting agent sold under the trademark AVANEL S-74 by the BASF Chemical Co. of Mt. Olive, N.J. AVANEL S-74 appears to be sulfate capped alkyl ethoxylate, where the wetting agent contains 3 units of ethoxylate and the alkyl is a C8 alkyl.

It is unclear how different wetting agents sometimes degrade the Cl+ moiety. It is felt that functional groups such as alkenes, alcohol, ketone, especially aliphatic ketones or aldehydes containing at least one alpha hydrogen next to the carbonyl carbon, and phenols as may be contained on the base wetting agent molecule are particularly harmful to the Cl+ moiety. Impurities as may be contained in various commercially available wetting agents can also play a significant part in the degradation of the Cl+ moiety. Some known degradative impurities are aromatic and conjugated phenols, compounds containing activated carbonyl, alpha aliphatic hydrogens, or active primary and secondary amines.

The concentration of the wetting agent in the biocidal solutions of the present application can be from about 0.05 to about 5%. In more specific embodiments, the concentration for the wetting agent is from about 0.5 to about 1.5%.

Another factor in choosing the concentration of the wetting agent is the degree to which it foams. If undesirable foaming occurs, anti foamers may be added to the solution.

The biocidal solution may further comprise a low molecular weight alcohol. The combination of sulfonamide and alcohol appears to synergistically enhance the biocidal effect of the solution. However, suitable alcohols are limited. Alcohols which do not contain hydrogen atoms alpha to the —OH moiety appear to offer more stable formulations. Alpha hydrogen atoms appear to reduce stability due to interaction with the active halogen contained in the active aromatic halo sulfonamide. Specific alcohols which are suitable for use include methanol and tertiary alcohols such as t-butanol [$C(CH_3)_3OH$]. In addition, t-butanol has a pleasant odor which may be pleasing to the consumer.

The alcohol can be present in the biocidal solution at concentrations of from about 0.1 to about 80%. In specific embodiments, the alcohol is present at a concentration of from about 0.1 to about 5.0%. In more specific embodiments, the alcohol is present at a concentration of from about 0.2 to about 1.0%.

The pH of the biocidal solution should be maintained within a range of from about 6.5 to about 10.0. In specific embodiments, the solution has a pH of from about 6.5 to about 9.5. In more specific embodiments, the solution has a pH of from about 7.0 to about 9.0. In still more specific embodiments, the solution has a pH of from about 7.5 to about 8.5. One consideration is the fact that aromatic N-halo active sulfonamide compounds exhibit excellent stability in a pH range of 8-9.5, which is important when long shelf life is very desirable.

Buffering agents may be used to maintain the pH within the desired range. They may also allow the active ingredients of the biocidal solution to be shipped in powdered form and mixed by the consumer with no adverse effect. Suitable buffering agents include sodium bicarbonate, potassium bicarbonate, sodium carbonate, potassium carbonate, acetate buffers (such as sodium acetate), phosphate buffers, pH blended phosphates, and sulfate buffers.

The concentration of the buffering agent can be from 0.1% up to the limit of solubility. The preferred range for the concentration of the buffering agent is from about 5% to about 200% of the active compound in solution. A more preferred range is from about 5% to about 50% with a most preferred concentration being 25-50%.

Unwanted troublesome microorganisms may be killed by various uses of the biocidal solution. A solution of the defined biocide may be sprayed onto an infected substrate. It can be wiped or swabbed onto an affected area. The solution can also be incorporated into a soap, lotion or the like. It could also be incorporated into a bath. Moreover, it may be incorporated into a medical device or dressing or related useful items.

The biocidal solution of the present application is illustrated by the following non-limiting examples, it being understood that these examples are intended to be illustrative only and that the present application is not intended to be limited to the materials, conditions, process parameters and the like recited herein. All proportions are by weight unless otherwise indicated.

EXAMPLES

In order to demonstrate the biocidal effects of the biocidal solution of the present application, a 1% aqueous solution of the sodium salt of Formula VI described above was sprayed on bacteria-laden test panels. The solution further contained 0.2% sodium bicarbonate and 0.03% of a wetting agent sold under the trademark AVANEL-S74. The exposure time and % kill of the test are set forth in Table I.

TABLE I

| Exposure Time | Organism (as % killed) | | | | | |
| --- | --- | --- | --- | --- | --- | --- |
| | Staph Epi | E. coli | VRE | MRSA | Pseudomonas | Strep A |
| 10 min | 100 | 100 | 100 | 100 | 100 | 100 |
| 5 min | 100 | 100 | 100 | 100 | 100 | 100 |
| 1 min | 99.6 | 100 | 91.4 | 99.2 | 100 | 72.1 |
| 30 sec | 88.7 | 100 | 81.4 | 91.2 | 100 | 68.9 |
| 5 sec | 8.1 | 86.9 | 40.9 | 66.7 | 55.1 | 59.5 |

Toxicity studies of N-chloro-4-carboxybenzene sulfonamide were also performed. In single dose oral toxicity studies with 10 rats using an aqueous solution of the compound, toxicity was determined to be greater than 5,000 mg/kg. In a skin irritation study conducted on rabbits using a formulation containing the compound, there was no incidence of irritation over 1, 24, 48, or 72 hour periods.

The aqueous solution comprising 1% of the sodium salt of Formula VI, 0.2% sodium bicarbonate and 0.03% AVANEL-S74 was then mixed with various alcohols to determine which alcohols best enhanced the biocidal effect of the solution. The alcohol was added at 1% concentration. The samples were held at room temperature for 3 days, then heated and held at 50° C. and checked periodically for active chlorine. The results are set forth in Table II as the % of active chlorine.

TABLE II

| | % Active Chlorine | | | | | | |
| --- | --- | --- | --- | --- | --- | --- | --- |
| | Time | | | | | | |
| | Initial | 7 days | 14 days | 21 days | 39 days | 63 days | % active chlorine remaining |
| Methanol | 0.21 | 0.191 | 0.17 | 0.16 | 0.12 | 0.09 | 43% |
| Isopropyl alcohol | 0.21 | 0.12 | 0.03 | 0.004 | 0 | 0 | 0 |
| Ethanol | 0.21 | 0.2 | 0.18 | 0.14 | 0.004 | 0 | 0 |
| t-butanol | 0.21 | 0.2 | 0.2 | 0.2 | 0.19 | 0.19 | 90% |
| 1-propanol | 0.21 | 0.1 | 0 | 0 | 0 | 0 | 0 |
| 1-butanol | 0.21 | 0.1 | 0 | 0 | 0 | 0 | 0 |
| phenol | 0.21 | 0 | 0 | 0 | 0 | 0 | 0 |

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A process for killing unwanted microorganisms on an affected area, comprising:
contacting the area with a biocidal solution comprising an effective amount of a halo active aromatic sulfonamide compound of the following Formula I:

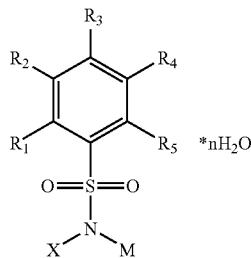

Formula I wherein
X is a halogen;
$R_3$ is methyl or COOM;
$R_1$, $R_2$, $R_4$, and $R_5$ are independently selected from hydrogen, $CF_3$, COOH, an ester or alkylated amide, COOM, CN, $NO_2$, $SO_3H$, a halogen, a substituted or unsubstituted phenyl group, a sulfonamide, a halosulfonamide, and a straight or branched aliphatic moiety from $C_1$ to $C_{12}$, wherein the same straight or branched aliphatic moiety may be substituted at one or more of the aliphatic hydrogens;
at least one of $R_1$, $R_2$, $R_4$ and $R_5$ is not hydrogen; and
M is an alkali or alkaline earth metal.

2. The process of claim 1, wherein the solution further comprises a wetting agent that essentially does not react with the sulfonamide compound.

3. The process of claim 2, where the wetting agent is a nonionic wetting agent.

4. The process of claim 2, wherein the concentration of the wetting agent in the biocidal solution is from about 0.05 to about 5%.

5. The process of claim 1, wherein the solution further comprises a low molecular weight alcohol.

6. The process of claim 5, wherein the alcohol is selected from methanol and t-butanol.

7. The process of claim 5, wherein the concentration of the alcohol in the biocidal solution is from about 0.1 to about 5.0%.

8. The process of claim 1, wherein the solution is buffered to a pH of from about 6.5 to about 10.0.

9. The process of claim 8, wherein the solution is buffered to a pH of from about 7.0 to about 9.0.

10. The process of claim 9, wherein the solution is buffered to a pH of from about 7.5 to about 8.5.

11. The process of claim 8, wherein the solution is buffered with sodium bicarbonate.

12. The process of claim 1, wherein the concentration of the sulfonamide compound in the biocidal solution is from about 0.1 to about 37%.

13. The process of claim 12, wherein the concentration of the sulfonamide compound in the biocidal solution is from about 0.1 to about 20%.

14. The process of claim 1, wherein the biocidal solution is incorporated into a soap, lotion, wipe, or swab which is then contacted with the affected area.

15. A process for killing unwanted microorganisms on an affected area, comprising: contacting the area with a biocidal solution comprising an effective amount of an N-halo-4-carboxybenzene sulfonamide of the following Formula V:

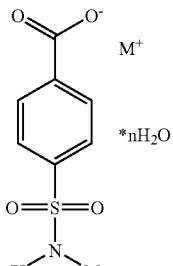

Formula V wherein X is a halogen; and
M is an alkali or alkaline earth metal.

16. The process of claim 15, wherein the sulfonamide compound is of the following Formula VI:

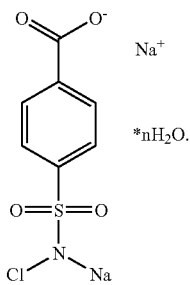

Formula VI

17. The process of claim 15, wherein the sulfonamide compound is of the following Formula VII:

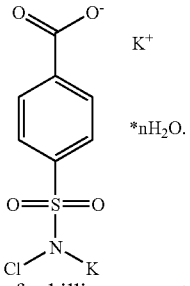

Formula VII

18. A process for killing unwanted microorganisms on an affected area, comprising contacting the area with a biocidal solution, wherein the solution comprises
an effective amount of a halo active aromatic sulfonamide compound of the following Formula V:

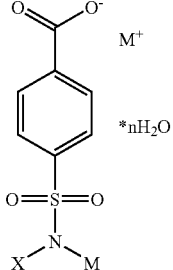

Formula V wherein X is a halogen; and M is an alkali or alkaline earth metal;
a wetting agent; and
an alcohol selected from methanol and t-butanol.

19. The process of claim 18, wherein the solution is buffered to a pH of from about 7.5 to about 8.5.

* * * * *